US012233208B2

(12) United States Patent
Lamb et al.

(10) Patent No.: US 12,233,208 B2
(45) Date of Patent: Feb. 25, 2025

(54) RADIO-FREQUENCY IDENTIFICATION (RFID) AUTHENTICATION SYSTEM FOR AEROSOL DELIVERY DEVICES

(71) Applicant: RAI STRATEGIC HOLDINGS, INC., Winston-Salem, NC (US)

(72) Inventors: Wilson Christopher Lamb, Hillsborough, NC (US); Raymond Charles Henry, Jr., Green Cove Springs, FL (US); Terrence E. Rogers, Chapel Hill, NC (US); Frederic Philippe Ampolini, Winston-Salem, NC (US)

(73) Assignee: RAI STRATEGIC HOLDINGS, INC., Winston-Salem, NC (US)

(*) Notice: Subject to any disclaimer, the term of this patent is extended or adjusted under 35 U.S.C. 154(b) by 207 days.

(21) Appl. No.: 17/235,503

(22) Filed: Apr. 20, 2021

(65) Prior Publication Data
US 2021/0236751 A1 Aug. 5, 2021

Related U.S. Application Data

(62) Division of application No. 14/808,466, filed on Jul. 24, 2015, now Pat. No. 11,033,054.

(51) Int. Cl.
*A61M 15/06* (2006.01)
*A24F 40/10* (2020.01)
(Continued)

(52) U.S. Cl.
CPC ............. *A61M 15/06* (2013.01); *A24F 40/40* (2020.01); *A24F 40/53* (2020.01); *A61M 11/042* (2014.02);
(Continued)

(58) Field of Classification Search
CPC ........ A24F 47/008; A24F 40/53; A24F 40/40; A24F 40/10; A61M 11/042; A61M 15/06; H04B 5/0037; H04B 5/0062
(Continued)

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

Sun, Pei-Liang, "Internet of Things of the Jail", Chapter 4 Radio Frequency Identification Technology, Huazhong University of Technology Press, Mar. 2012, 14 pages.
(Continued)

*Primary Examiner* — Steven W Crabb
*Assistant Examiner* — Alba T Tosario-Aponte
(74) *Attorney, Agent, or Firm* — Womble Bond Dickinson (US) LLP

(57) ABSTRACT

A control body and cartridge that are coupleable with one another to form an aerosol delivery device are provided. The control body comprises a control component and an RFID reader contained within at least one housing. The cartridge comprises at least one heating element and an RFID tag contained within at least one housing. The RFID reader of the control body is coupled to the control component of the control body and configured to communicate with the RFID tag of the cartridge upon coupling of the control body with the cartridge. The control component of the control body is configured to authorize the cartridge for use with the control
(Continued)

body based at least in part on communication between the RFID reader and the RFID tag.

10 Claims, 6 Drawing Sheets

(51) Int. Cl.
    *A24F 40/40*     (2020.01)
    *A24F 40/53*     (2020.01)
    *A61M 11/04*     (2006.01)
    *A61M 15/00*     (2006.01)
    *A61M 16/00*     (2006.01)
    *H04B 5/00*     (2024.01)
    *H04B 5/77*     (2024.01)
    *H04B 5/79*     (2024.01)

(52) U.S. Cl.
    CPC .............. *H04B 5/77* (2024.01); *H04B 5/79* (2024.01); *A24F 40/10* (2020.01); *A61M 15/008* (2014.02); *A61M 15/0081* (2014.02); *A61M 15/0083* (2014.02); *A61M 2016/0024* (2013.01); *A61M 2016/0039* (2013.01); *A61M 2205/127* (2013.01); *A61M 2205/14* (2013.01); *A61M 2205/27* (2013.01); *A61M 2205/3368* (2013.01); *A61M 2205/3592* (2013.01); *A61M 2205/3653* (2013.01); *A61M 2205/6018* (2013.01); *A61M 2205/6054* (2013.01); *A61M 2205/8212* (2013.01)

(58) Field of Classification Search
    USPC ......................................... 392/387, 386, 390
    See application file for complete search history.

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0200492 A1 | 10/2004 | Brooks |
| 2004/0203478 A1 | 10/2004 | Scott |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0194932 A1 | 8/2007 | Oishi et al. |
| 2007/0215167 A1 | 9/2007 | Crooks et al. |
| 2007/0282482 A1* | 12/2007 | Beucher .............. G06Q 10/08 700/226 |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0120431 A1 | 5/2009 | Borgschutte et al. |
| 2009/0126745 A1 | 5/2009 | Hon |
| 2009/0188490 A1 | 7/2009 | Hon |
| 2009/0195215 A1 | 8/2009 | Sato et al. |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |

(56) References Cited

U.S. PATENT DOCUMENTS

| | | |
|---|---|---|
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0206243 A1* | 8/2012 | Butler .............. H04B 5/0062 340/10.51 |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0220315 A1 | 8/2013 | Conley et al. |
| 2013/0255702 A1 | 10/2013 | Griffith, Jr. et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0338685 A1 | 11/2014 | Amir |
| 2014/0345631 A1 | 11/2014 | Bowen et al. |
| 2015/0053217 A1 | 2/2015 | Steingraber et al. |
| 2015/0136158 A1* | 5/2015 | Stevens ............... A24F 40/53 131/329 |
| 2016/0261021 A1* | 9/2016 | Marion ............... A24F 40/65 |

FOREIGN PATENT DOCUMENTS

| | | |
|---|---|---|
| CA | 2984161 | 11/2016 |
| CA | 2984364 | 11/2016 |
| CA | 2986167 | 11/2021 |
| CN | 1541577 | 11/2004 |
| CN | 2719043 | 8/2005 |
| CN | 2881791 | 3/2007 |
| CN | 200997909 | 1/2008 |
| CN | 101116542 | 2/2008 |
| CN | 101176805 | 5/2008 |
| CN | 101635393 | 1/2010 |
| CN | 201379072 | 1/2010 |
| CN | 201491279 | 5/2010 |
| CN | 203446536 | 2/2014 |
| CN | 103932406 | 7/2014 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 1 772 166 | 4/2007 |
| EP | 2 316 286 | 5/2011 |
| EP | 2 399 636 | 12/2011 |
| EP | 2862457 | 4/2015 |
| GB | 2469850 | 11/2010 |
| WO | WO 1997/48293 | 12/1997 |
| WO | WO 2003/034847 | 5/2003 |
| WO | WO 03/059424 | 7/2003 |
| WO | WO 2004/043175 | 5/2004 |
| WO | WO 2004/080216 | 9/2004 |
| WO | WO 2005/099494 | 10/2005 |
| WO | WO 2007/035913 | 3/2007 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2011/154276 | 12/2011 |
| WO | WO 2012/072762 | 6/2012 |
| WO | WO 2012/100523 | 8/2012 |
| WO | WO 2013/030117 | 3/2013 |
| WO | WO 2013/089551 | 6/2013 |
| WO | WO 2014/150247 | 9/2014 |

OTHER PUBLICATIONS

International Search Report dated Oct. 5, 2016 in the corresponding International Application No. PCT/US2016/043257.

\* cited by examiner

```
                                    ┌─ 500
                                    ▼

┌──────────┐
                              │  START   │
                              └────┬─────┘
                                   │
                                   ▼
┌──────────────────────────────────────────────────────────────────┐
│  A HEATING ELEMENT ACTIVATING TO VAPORIZE COMPONENTS OF AN AEROSOL│
│  PRECURSOR COMPOSITION IN RESPONSE TO A FLOW OF AIR THROUGH THE  │
│  AEROSOL DELIVERY DEVICE, THE AIR BEING COMBINABLE WITH A THEREBY│
│            FORMED VAPOR TO FORM AN AEROSOL                       │
│                            502                                    │
└──────────────────────────────┬───────────────────────────────────┘
                               │
                               ▼
┌──────────────────────────────────────────────────────────────────┐
│  AN RFID TAG COMMUNICATING WITH AN RFID READER OF A CONTROL BODY │
│  UPON COUPLING OF THE CARTRIDGE WITH THE CONTROL BODY, THE CARTRIDGE│
│  BEING AUTHORIZED AT AND FOR USE WITH THE CONTROL BODY BASED AT LEAST│
│   IN PART ON COMMUNICATION BETWEEN THE RFID READER AND THE RFID TAG │
│                            504                                    │
└──────────────────────────────┬───────────────────────────────────┘
                               │
                               ▼
                         ┌──────────┐
                         │   END    │
                         └──────────┘
```

FIG. 5

RADIO-FREQUENCY IDENTIFICATION (RFID) AUTHENTICATION SYSTEM FOR AEROSOL DELIVERY DEVICES

CROSS-REFERENCE TO RELATED APPLICATIONS

The present application is a divisional of U.S. patent application Ser. No. 14/808,466, filed Jul. 24, 2015, entitled: Radio-Frequency Identification (RFID) Authentication System for Aerosol Delivery Devices, the content of which is hereby incorporated by reference.

TECHNOLOGICAL FIELD

The present disclosure relates to aerosol delivery devices such as smoking articles that may utilize electrically generated heat for the production of aerosol (e.g., smoking articles commonly referred to as electronic cigarettes), and more particularly to aerosol delivery devices that utilize radio-frequency identification (RFID) as a means for authenticating various components of the aerosol delivery for usage with one another. The smoking articles may be configured to heat an aerosol precursor, which may incorporate materials that may be made or derived from, or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., all of which are incorporated herein by reference in their entireties. See also, for example, the various types of smoking articles, aerosol delivery devices and electrically-powered heat generating sources referenced by brand name and commercial source in U.S. patent application Ser. No. 14/170,838 to Bless et al., filed Feb. 3, 2014, which is incorporated herein by reference in its entirety. Additionally, other types of smoking articles have been proposed in U.S. Pat. No. 5,505,214 to Collins et al., U.S. Pat. No. 5,894,841 to Voges, U.S. Pat. No. 6,772,756 to Shayan, U.S. Pat. App. Pub. No. 2006/0196518 to Hon, and U.S. Pat. App. Pub. No. 2007/0267031 to Hon, all of which are incorporated herein by reference in their entireties.

Ongoing developments in the field of aerosol delivery devices have resulted in increasingly sophisticated aerosol delivery devices. For example, some aerosol delivery devices utilize authentication methods to ensure that components of the aerosol delivery device are authorized for usage with one another. However, the current authentication methods require the usage of cartridge memory that, in some instances, results in higher manufacturing cost. Furthermore, the current methods require the usage of external components in the cartridge, such as a connector pin, to enable cartridge communication. Therefore, a need exist for an authentication method that eliminates the need of external components and separate memory to facilitate device authentication.

BRIEF SUMMARY

The present disclosure relates to aerosol delivery devices, methods of forming such devices, and elements of such devices. The present disclosure thus includes, without limitation, the following example implementations. In some example implementations, a control body is provided that is coupleable with a cartridge equipped with a heating element and contains an aerosol precursor composition, and further equipped with a radio-frequency identification (RFID) tag. The control body is coupleable with the cartridge to form an aerosol delivery device in which the heating element is configured to activate and vaporize components of the aerosol precursor composition.

The control body comprises at least one housing; and contained within the at least one housing, a control component configured to control operation of at least one functional element of the aerosol delivery device based on a detected flow of air through at least a portion of the aerosol delivery device; and an RFID reader coupled to the control component and configured to communicate with the RFID tag of the cartridge upon coupling of the control body with the cartridge, the control component being configured to authorize the cartridge for use with the control body based at least in part on communication between the RFID reader and the RFID tag.

In some example implementations of the control body of the preceding or any subsequent example implementation, or any combination thereof, the RFID reader includes an antenna and is contained within the at least one housing such that upon coupling of the control body with the cartridge, the antenna is located proximate a corresponding antenna of the RFID tag to enable the communication between the RFID reader and the RFID tag. The antenna of the RFID reader is up to two millimeters in length to render the RFID reader substantially incapable of communication with any device external to the control body other than the RFID tag.

In some example implementations of the control body of any preceding or any subsequent example implementation, or any combination thereof, the communication between the RFID reader and the RFID tag includes an authentication indicia communicated from the RFID tag to the RFID reader. The control component being configured to authorize the cartridge includes being configured to automatically receive the authentication indicia from the RFID tag via the RFID reader upon coupling the control body with the cartridge, and automatically evaluate the authentication indicia to determine whether the cartridge is authorized for use with the control body, the cartridge in at least one instance being authorized for use with the control body.

In some example implementations of the control body of any preceding or any subsequent example implementation, or any combination thereof, the control component is configured to enable current flow and thereby activation of the heating element in the at least one instance in which the cartridge is authorized for use with the control body, and prohibit the current flow and thereby activation of the heating element in at least one other instance in which the cartridge is unauthorized for use with the control body.

In some example implementations of the control body of any preceding or any subsequent example implementation, or any combination thereof, the RFID reader includes an antenna and a radio-frequency amplifier configured to drive the antenna. The radio-frequency amplifier is configured to operate at a power level of at least one-hundred milliwatts to enable an emission of energy sufficient to at least partially power the RFID tag.

In some example implementations, a cartridge is provided that is coupleable with a control body equipped with a radio-frequency identification (RFID) reader. The cartridge is coupleable with the control body to form an aerosol delivery device. The cartridge comprises at least one housing; and contained within the at least one housing, a heating element configured to activate and vaporize components of an aerosol precursor composition in response to a flow of air through the aerosol delivery device, the air being combinable with a thereby formed vapor to form an aerosol; and an RFID tag configured to communicate with the RFID reader of the control body upon coupling of the cartridge with the control body, the control body being configured to authorize the cartridge for use with the control body based at least in part on communication between the RFID tag and the RFID reader.

In some example implementations of the cartridge of the preceding or any subsequent example implementation, or any combination thereof, the RFID tag includes an antenna and is contained within the at least one housing such that upon coupling of the control body with the cartridge, the antenna is located proximate a corresponding antenna of the RFID reader to enable the communication between the RFID reader and the RFID tag. The antenna of the RFID tag is up to two millimeters in length to render the RFID tag substantially incapable of communication with any device external to the cartridge other than the RFID reader.

In some example implementations of the cartridge of any preceding or any subsequent example implementation, or any combination thereof, the communication between the RFID tag and the RFID reader includes an authentication indicia communicated from the RFID tag to the RFID reader. The RFID tag is configured to automatically communicate the authentication indicia to the RFID reader upon coupling of the control body with the cartridge. The control body being configured to authorize the cartridge includes a control component of the control body being configured to receive the authentication indicia from the RFID tag via the RFID reader, and evaluate the authentication indicia to determine whether the cartridge is authorized for use with the control body, the cartridge in at least one instance being authorized for use with the control body.

In some example implementations of the cartridge of any preceding or any subsequent example implementation, or any combination thereof, the control component is configured to enable current flow and thereby activation of the heating element in the at least one instance in which the cartridge is authorized for use with the control body, and prohibit the current flow and thereby activation of the heating element in at least one other instance in which the cartridge is unauthorized for use with the control body.

In some example implementations of the cartridge of any preceding or any subsequent example implementation, or any combination thereof, the cartridge is a disposable cartridge with flavor-containing aerosol precursor composition, and the RFID tag includes a memory configured to store information related to a capacity of the cartridge or flavor of the flavor-containing aerosol precursor composition, and store data related to a puff count associated with the cartridge.

In some example implementations, a method is provided for operation of a control body coupleable with a cartridge that is equipped with a heating element and contains an aerosol precursor composition, and that is further equipped with a radio-frequency identification (RFID) tag. The control body is coupleable with the cartridge to form an aerosol delivery device in which the heating element is configured to activate and vaporize components of the aerosol precursor composition. The method comprising at the control body a control component controlling operation of at least one functional element of the aerosol delivery device based on a detected flow of air through at least a portion of the aerosol delivery device, an RFID reader communicating with the RFID tag of the cartridge upon coupling of the control body with the cartridge, and the control component authorizing the cartridge for use with the control body based at least in part on communication between the RFID reader and the RFID tag.

In some example implementations of the method of the preceding or any subsequent example implementation, or any combination thereof, the RFID reader includes an antenna such that upon coupling of the control body with the cartridge, the antenna is located proximate a corresponding antenna of the RFID tag to enable the communication between the RFID reader and the RFID tag, and the antenna of the RFID reader is up to two millimeters in length to render the RFID reader substantially incapable of communication with any device external to the control body other than the RFID tag.

In some example implementations of the method of any preceding or any subsequent example implementation, or any combination thereof, the communication between the RFID reader and the RFID tag includes an authentication indicia communicated from the RFID tag to the RFID reader. The control component authorizing the cartridge includes automatically receiving the authentication indicia from the RFID tag via the RFID reader upon coupling the control body with the cartridge, and automatically evaluating the authentication indicia to determine whether the cartridge is authorized for use with the control body, the cartridge in at least one instance being authorized for use with the control body.

In some example implementations of the method of any preceding or any subsequent example implementation, or any combination thereof, the method further comprises the control component enabling current flow and thereby activation of the heating element in the at least one instance in which the cartridge is authorized for use with the control body, and prohibiting the current flow and thereby activation of the heating element in at least one other instance in which the cartridge is unauthorized for use with the control body.

In some example implementations of the method of any preceding or any subsequent example implementation, or any combination thereof, the RFID reader includes an antenna and a radio-frequency amplifier driving the antenna, the method further comprising the radio-frequency amplifier operating at a power level of at least one-hundred milliwatts to enable an emission of energy sufficient to at least partially power the RFID tag.

In some example implementations, a method is provided for operation of a cartridge coupleable with a control body equipped with a radio-frequency identification (RFID) reader. The cartridge being coupleable with the control body to form an aerosol delivery device, and the method comprises at the cartridge a heating element activating to vaporize components of an aerosol precursor composition in response to a flow of air through the aerosol delivery device, the air being combinable with a thereby formed vapor to form an aerosol; and an RFID tag communicating with the RFID reader of the control body upon coupling of the cartridge with the control body, the cartridge being authorized at and for use with the control body based at least in part on communication between the RFID reader and the RFID tag.

In some example implementations of the method of the preceding or any subsequent example implementation, or any combination thereof, the RFID tag includes an antenna and is contained within the at least one housing such that upon coupling of the control body with the cartridge, the antenna is located proximate a corresponding antenna of the RFID reader to enable the communication between the RFID reader and the RFID tag. The antenna of the RFID tag is up to two millimeters in length to render the RFID tag substantially incapable of communication with any device external to the cartridge other than the RFID reader.

In some example implementations of the method of any preceding or any subsequent example implementation, or any combination thereof, the communication between the RFID tag and the RFID reader includes an authentication indicia communicated from the RFID tag to the RFID reader, and the method further comprises the RFID tag automatically communicating the authentication indicia to the RFID reader upon coupling of the control body with the cartridge. The cartridge being authorized includes a control component of the control body receiving the authentication indicia from the RFID tag via the RFID reader, and evaluating the authentication indicia to determine whether the cartridge is authorized for use with the control body, the cartridge in at least one instance being authorized for use with the control body.

In some example implementations of the method of any preceding or any subsequent example implementation, or any combination thereof, current flow and thereby activation of the heating element is enabled by the control component in the at least one instance in which the cartridge is authorized for use with the control body, and prohibited in at least one other instance in which the cartridge is unauthorized for use with the control body.

In some example implementations of the method of any preceding or any subsequent example implementation, or any combination thereof, the cartridge is a disposable cartridge with flavor-containing aerosol precursor composition, and the RFID tag includes a memory. The method further comprises at the memory storing information related to a capacity of the cartridge or flavor of the flavor-containing aerosol precursor composition, and storing data related to a puff count associated with the cartridge.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

FIG. 5 illustrates various operations in a method of operation of an aerosol delivery device cartridge, according to an example implementation of the present disclosure.

DETAILED DESCRIPTION

Figure 1:
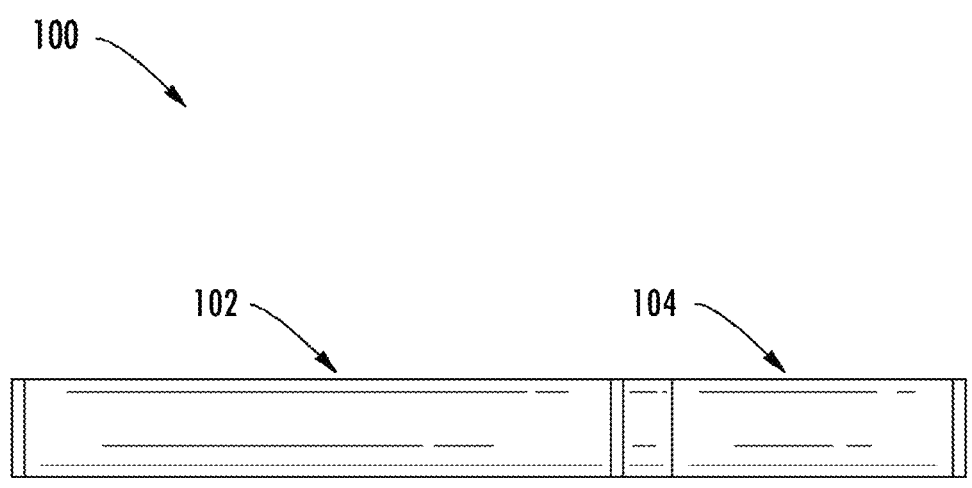
FIG. 1 illustrates a side view of an aerosol delivery device including a cartridge coupled to a control body, according to an example implementation of the present disclosure.

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., a rechargeable battery and various electronics for controlling the operation of that article), and at the other end and integral with or removably coupled thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouth end region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be permanently or detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The cartridge and control body may include a unitary housing or outer body or separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic and the like.

In some example implementations, one or both of the control body 102 or the cartridge 104 of the aerosol delivery device 100 may be referred to as being disposable or as being reusable. For example, the control body may have a replaceable battery or a rechargeable battery and thus may be combined with any type of recharging technology, including connection to a typical alternating current electrical outlet, connection to a car charger (i.e., a cigarette lighter receptacle), and connection to a computer, such as through a universal serial bus (USB) cable or connector. Further, in some example implementations, the cartridge may comprise a single-use cartridge, as disclosed in U.S. Pat. No. 8,910,639 to Chang et al., which is incorporated herein by reference in its entirety.

In one example implementation, the control body 102 and cartridge 104 forming the aerosol delivery device 100 may be permanently coupled to one another. Examples of aerosol delivery devices that may be configured to be disposable and/or which may include first and second outer bodies that are configured for permanent coupling are disclosed in U.S. patent application Ser. No. 14/170,838 to Bless et al., filed Feb. 3, 2014, which is incorporated herein by reference in its entirety. In another example implementation, the cartridge and control body may be configured in a single-piece, non-detachable form and may incorporate the components, aspects, and features disclosed herein. However, in another example implementation, the control body and cartridge may be configured to be separable such that, for example, the cartridge may be refilled or replaced.

Figure 2A:
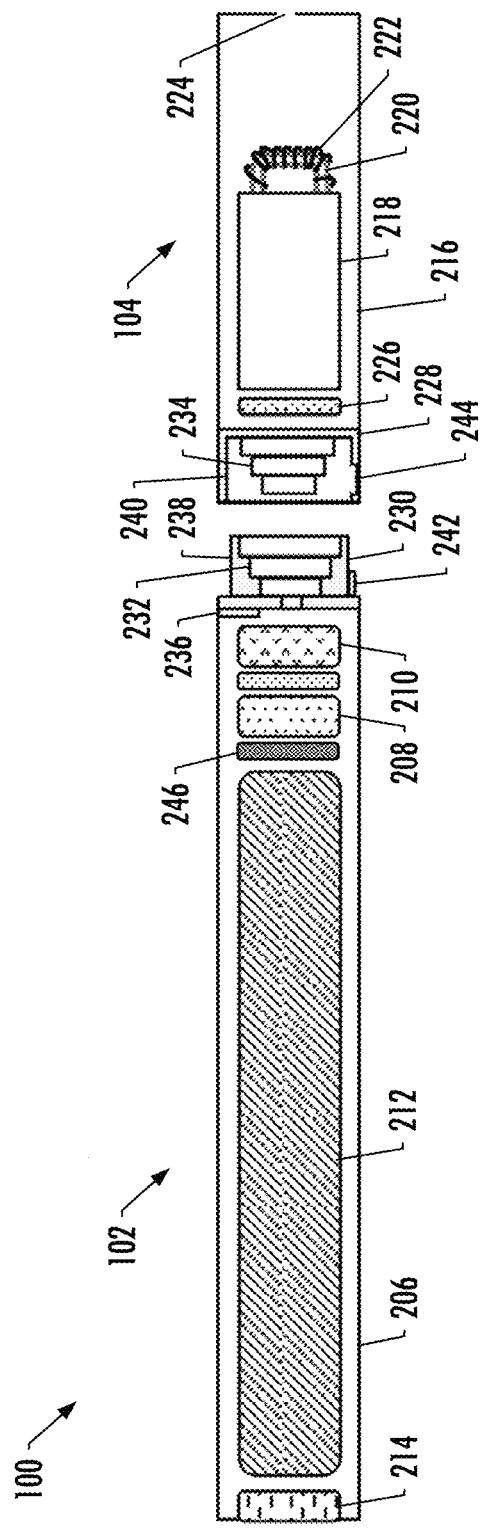
FIG. 2A is a partially cut-away view of an aerosol delivery device that according to various example implementations may correspond to the aerosol delivery device of FIG. 1.

FIG. 2A illustrates a more particular example implementation of the aerosol delivery device 100. As seen in the cut-away view illustrated therein, the aerosol delivery device can comprise a control body 102 and cartridge 104. As illustrated in FIG. 2A, the control body can be formed of a control body shell 206 that can include a control component 208 (e.g., a microprocessor, individually or as part of a microcontroller), a flow sensor 210, a battery 212, and one or more light-emitting diodes (LEDs) 214, and such components may be variably aligned. Further indicators (e.g., a haptic feedback component, an audio feedback component, or the like) can be included in addition to or as an alternative to the LED. The cartridge can be formed of a cartridge shell 216 enclosing a reservoir 218 that is in fluid communication with a liquid transport element 220 adapted to wick or otherwise transport an aerosol precursor composition stored in the reservoir housing to a heater 222 (sometimes referred to as a heating element). In some example, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 222. The heater in these examples may be resistive heating element such as a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 2A as described herein.

An opening 224 may be present in the cartridge shell 216 (e.g., at the mouthend) to allow for egress of formed aerosol from the cartridge 104. Such components are representative of the components that may be present in a cartridge and are not intended to limit the scope of cartridge components that are encompassed by the present disclosure.

The cartridge 104 also may include one or more electronic components 226, which may include an integrated circuit, a memory component, a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that the control component and the flow sensor may be combined as an electronic circuit board with the air flow sensor attached directly thereto. Further, the electronic circuit board may be positioned horizontally relative to the illustration of FIG. 1 in that the electronic circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate as further described below.

The control body 102 and the cartridge 104 may include components adapted to facilitate a fluid engagement therebetween. As illustrated in FIG. 2A, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the battery 212 and control component 208 in the control body and the heater 222 in the cartridge. Further, the control body shell 206 can include an air intake 236, which may be a notch in the shell where it connects to the coupler that allows for passage of ambient air around the coupler and into the shell where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference in its entirety. For example, the coupler 230 as seen in FIG. 2A may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 218 illustrated in FIG. 2A can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 220. The liquid transport element can transport the aerosol precursor composition stored in the reservoir via capillary action to the heater 222 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 2A as described herein. In particular, specific combinations of heating members and transport elements as further described below may be incorporated into devices such as illustrated in FIG. 2A as described herein.

In use, when a user draws on the aerosol delivery device 100, airflow is detected by the flow sensor 210, and the heater 222 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heater and out the opening 224 in the mouthend of the aerosol delivery device.

In some examples, the aerosol delivery device 100 may include a number of additional software-controlled functions. For example, the aerosol delivery device may include a battery protection circuit configured to detect battery input, loads on the battery terminals, and charging input. The battery protection circuit may include short-circuit protection and under-voltage lock out. The aerosol delivery device may also include components for ambient temperature measurement, and its control component 208 may be configured to control at least one functional element to inhibit battery charging if the ambient temperature is below a certain temperature (e.g., 0° C.) or above a certain temperature (e.g., 45° C.) prior to start of charging or during charging.

Power delivery from the battery 212 may vary over the course of each puff on the device 100 according to a power control mechanism. The device may include a "long puff" safety timer such that in the event that a user or an inadvertent mechanism causes the device to attempt to puff continuously, the control component 208 may control at least one functional element to terminate the puff automatically after some period of time (e.g., four seconds). Further, the time between puffs on the device may be restricted to less than a period of time (e.g., 100). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 100 may include a puff tracking algorithm configured for heater lockout once a defined number of puffs has been achieved for an attached cartridge (based on the number of available puffs calculated in light of the e-liquid charge in the cartridge). In some implementations, the puff tracking algorithm indirectly counts the number of puffs based on a corresponding number of puff seconds. As such, the puff tracking algorithm may incrementally count a number of puff seconds in order to calculate when a specified number of puffs have occurred and subsequently shut off the device once the puff seconds reach what is estimated to be a pre-determined number of puffs. For example, if three (3) seconds is defined to be equivalent to one "average" puff and the device have been configured to shut down after two hundred (200) average puffs, the device may shut down after six hundred (600) puff second have elapsed with respect to usage of the cartridge. The puff tracking algorithm may further estimate the amount of e-liquid that is utilized per puff second, and mathematically calculate the e-liquid volume based at least in part on the estimation of corresponding puffs seconds.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference in its entirety.

The aerosol delivery device 100 can incorporate the sensor 210 or another sensor or detector for control of supply of electric power to the heater 222 when aerosol generation is desired (e.g., upon draw during use). As such, for example, there is provided a manner or method of turning off the power supply to the heater when the aerosol delivery device is not be drawn upon during use, and for turning on the power supply to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 100 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al., U.S. Pat. No. 5,101,839 to Jakob et al., U.S. Pat. No. 6,779,531 to Biggs et al., U.S. Pat. App. Pub. No. 2013/0008457 to Zheng et al., and Chemical and Biological Studies on New Cigarette Prototypes that Heat Instead of Burn Tobacco, R. J. Reynolds Tobacco Company Monograph (1988), all of which are incorporated herein by reference in their entireties.

Additional representative types of components that yield visual cues or indicators may be employed in the aerosol delivery device 100, such as LEDs and related components, auditory elements (e.g., speakers), vibratory elements (e.g., vibration motors) and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2014/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

The control component 208 includes a number of electronic components, and in some examples may be formed of a printed circuit board (PCB) that supports and electrically connects the electronic components. Examples of suitable electronic components include a microprocessor or processor core, an integrated circuit, a memory, and the like. In some examples, the control component may include a microcontroller with an integrated processor core and memory, and which may further include one or more integrated input/output peripherals.

The aerosol delivery device 100 may further include a communication interface 246 coupled to the control component 208, and which may be configured to enable wireless communication. In some examples, the communication interface may be included on the PCB of the control component, or a separate PCB that may be coupled to the PCB or one or more components of the control component. The communication interface may enable the aerosol delivery device to wirelessly communicate with one or more networks, computing devices or other appropriately-enabled devices. Examples of suitable computing devices include any of a number of different mobile computers. More particular examples of suitable mobile computers include portable computers (e.g., laptops, notebooks, tablet computers), mobile phones (e.g., cell phones, smartphones), wearable computers (e.g., smartwatches) and the like. In other examples, the computing device may be embodied as other than a mobile computer, such as in the manner of a desktop computer, server computer or the like. And in yet another example, the computing device may be embodied as an electric beacon such as one employing iBeacon™ technology developed by Apple Inc. Examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

The communication interface 246 may include, for example, an antenna (or multiple antennas) and supporting hardware and/or software for enabling wireless communication with a communication network (e.g., a cellular network, Wi-Fi, WLAN, and/or the like), and/or for supporting device-to-device, short-range communication, in accordance with one or more desired communication technologies. The communication interface may at times be composed of multiple separate or integrated communication interfaces enabling communication in accordance with multiple communication technologies. Examples of suitable short-range communication technologies that may be supported by the communication interface include various near field communication (NFC) technologies, wireless personal area network (WPAN) technologies and the like. More particular examples of suitable WPAN technologies include those specified by IEEE 802.15 standards or otherwise, including Bluetooth, Bluetooth low energy (Bluetooth LE), ZigBee, infrared (e.g., IrDA), radio-frequency identification (RFID), Wireless USB and the like. Yet other examples of suitable short-range communication technologies include Wi-Fi Direct, as well as certain other technologies based on or specified by IEEE 802.11 standards and that support direct device-to-device communication.

In some example implementations, the aerosol delivery device 100 may utilize RFID authentication as a means for authenticating various components of the device, such as the control body 102 and cartridge 104, for usage with one another. To further illustrate aspects of example implementations of the present disclosure, reference is now made to FIGS. 3-5 which illustrate various components for use within a suitable aerosol delivery device, and more particularly for use in authenticating individual components of the suitable aerosol delivery device, and methods for operation of the various components.

Figure 3:
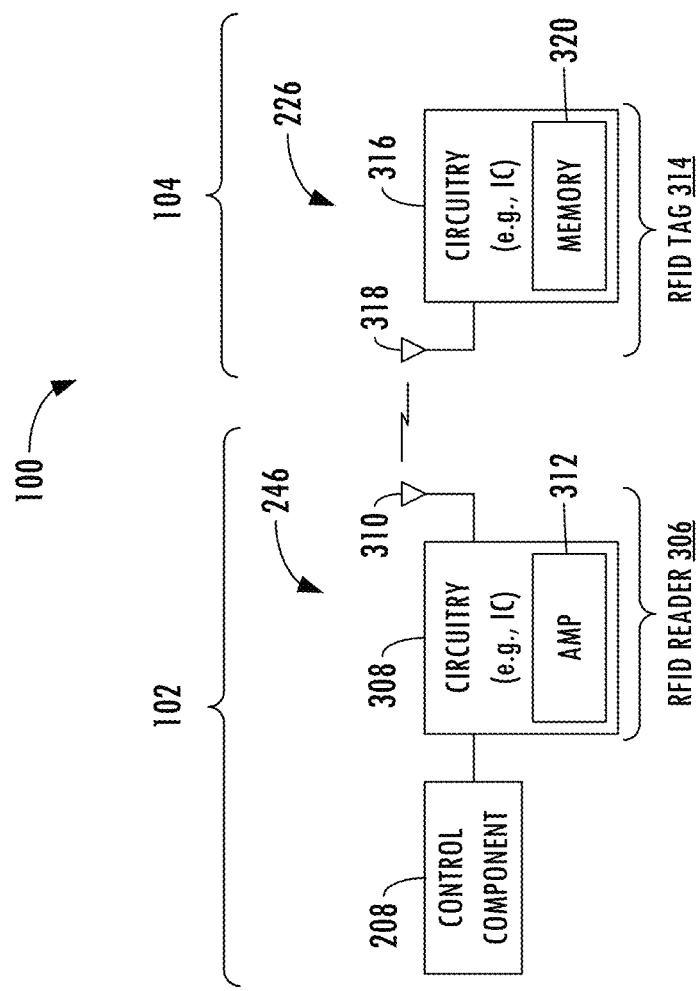
FIG. 3 illustrates an example configuration of various electronic components that may be within a suitable aerosol delivery device to implement RFID authentication, according to example implementations.

FIG. 3 even more particularly illustrates various components of the aerosol delivery device 100. As shown, the aerosol delivery device may include a control body 102 and cartridge 104. In some example implementations, the control body may be coupleable with the cartridge to form the aerosol delivery device.

As shown, the control body 102 may comprise a communication interface 246 that may be or include an RFID reader 306. The RFID reader may include circuitry 308, such as an integrated circuit (IC), coupled to an antenna 310, and having at least an amplifier 312 therein. The communication interface, and more particularly the RFID reader, may be coupled to a control component 208. The control component may be configured to control operation of at least one functional element of the aerosol delivery device 300 based on a detected flow of air through at least a portion of the aerosol delivery device. In some example implementations, the control component may be further coupled to an additional component of the communication interface such a Bluetooth device.

In one example implementation, the amplifier 312 (e.g., a radio-frequency amplifier) is configured to drive the antenna 310. The amplifier may also be configured to operate at a sufficient power level (e.g., at least one-hundred milliwatts) to enable an emission of energy sufficient to at least partially power an RFID tag 314 within the cartridge 104 upon coupling of the control body 102 with the cartridge. It should be noted that in other implementations, the amplifier may be configured to operate at a power level not explicitly expressed herein. For example, in one example implementation, the amplifier may also be configured to operate at a lower power level (e.g., less than one-hundred milliwatts). In some example implementations, the amplifier may be configured to operate within a constrained power level range (e.g., 10-20 milliwatts). In one implementation, for example, the amplifier may be configured to operate up to a predetermined number of milliwatts (e.g., 100 milliwatts).

As further shown, the cartridge 104 may comprise one or more electronic components 226 that may be or include an RFID tag 314 configured to communicate with the RFID reader 306 of the control body upon coupling of the cartridge with the control body. The RFID tag may include circuitry 316 (e.g., IC) coupled to an antenna 318, and having at least a memory component 320 therein. In some example implementations, the control body 102, and more particularly the control component 208, may be configured to authorize the cartridge 104 for use with the control body based at least in part on communication between the RFID reader and the RFID tag.

In one example implementation, the cartridge 104 may be a disposable cartridge with flavor-containing aerosol precursor composition such that the memory component 320 may be configured to store information including, but not limited to, a capacity of the cartridge or flavor of the flavor-containing aerosol precursor composition. For example, the memory component may be further configured to store data related to a puff count associated with the cartridge.

As previously indicated, the RFID reader 306 and the RFID tag 314 may include and/or be coupled with separate and distinct antennas 310, 318, respectively, in which that antennas may facilitate short-range communication between the RFID reader and the RFID tag. For example, the antenna 310 of the RFID reader may be contained within the housing of the control body 102 and coupled to the circuitry 308 of the RFID reader such that upon coupling of the control body with the cartridge 104, the antenna is located proximate a corresponding antenna 318 of the RFID tag to enable the communication between the RFID reader and the RFID tag.

Figure 2B:
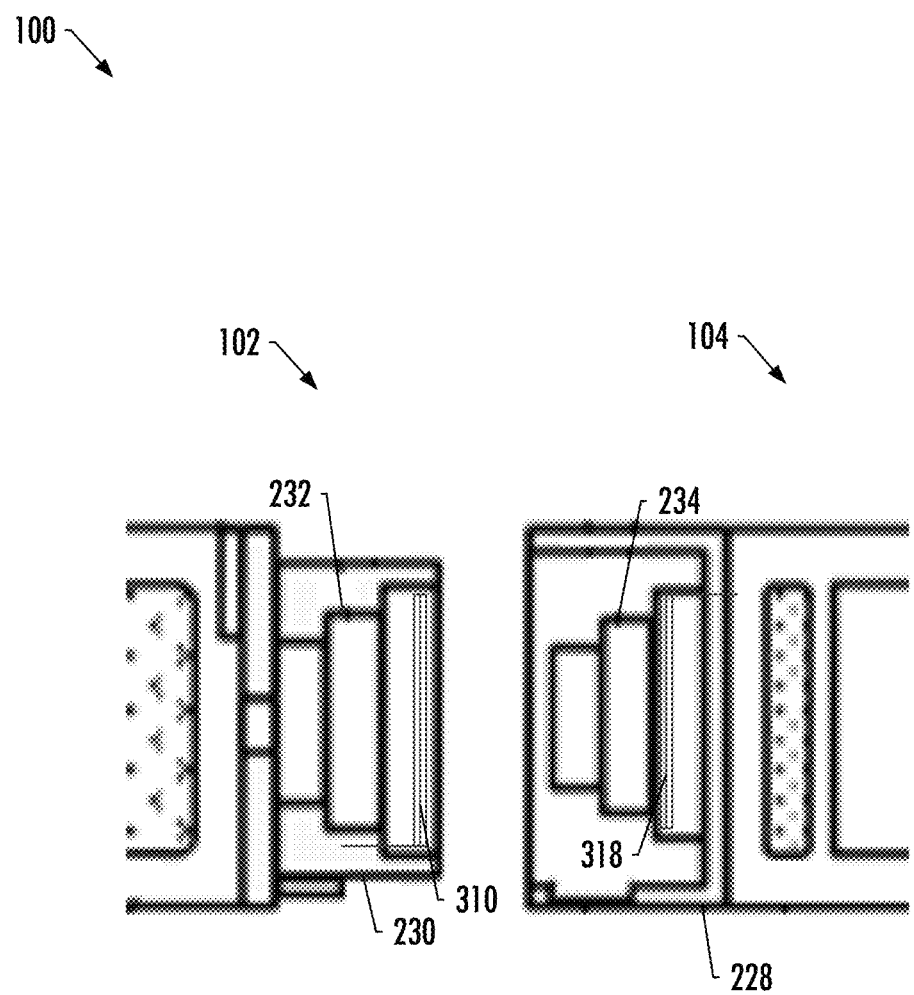
FIG. 2B illustrates an exploded view of a portion of the aerosol delivery device of FIG. 2A, according to an example implementation of the present disclosure.

As previously indicated, and further shown in FIG. 2B, the control body 102 may include a coupler 230 having a cavity 232 therein in which the RFID antenna may be positioned, and the cartridge 104 may include a base 228 having a projection 234 on which the RFID antenna may be positioned such that the antennas are coaxially aligned upon coupling of the coupler 230 and the base 228 and thereby proximate to one another. In some examples, the cavity and the projection may comprise three radially-spaced tiers each having a corresponding electrical connection therein. In one example implementations, the antennas may be positioned on a single tier adjacent to the corresponding electrical connection. In another example implementation, the placement of the antenna within the tier may eliminate the need of the electrical connection thereby increasing reliability of the aerosol delivery device 100 and decreasing manufacturing cost associated with the aerosol delivery device.

In some example implementations, the antenna 310 of the RFID reader 306 may be coupled to the amplifier 312 and a transmitter within the circuitry of the RFID reader. The transmitter of the RFID reader may be or include a circuitry component capable of transmitting and modulating radio waves to communicate data via the RFID reader to the RFID tag 314. The transmitter may be implemented alongside a protocol controller that may provide data to the transmitter for subsequent communication in which the data may be received from the control component 208. As such, in some example implementations, the control component is operatively coupled to the circuitry of the RFID reader via the protocol controller.

The antenna 318 of the RFID tag 314 may be contained within the housing of the cartridge 104 and coupled to the circuitry 316 of the RFID tag such that upon coupling of the control body 102 with the cartridge, the antenna is located proximate the corresponding antenna 310 of the RFID reader 306 to enable the communication between the RFID reader and the RFID tag. In some example implementations, the antenna of the RFID reader may be coupled to a receiver within the circuitry of the RFID reader via one or more electronic components (e.g., a diode, a transistor, an optoelectronic device, a resistor, a capacitor, a switch, and the like).

The receiver of the RFID tag 314 may receive the modulated signal communicated by the RFID reader 306 (e.g., communicated by a transmitter of the RFID reader) via the antenna 310, and thereby demodulate the signal. Examples of suitable receivers may be, or include, superheterodyne receivers and super-regenerative receivers. The receiver may be implemented alongside a protocol controller of the RFID tag that may receive an/or provide data to the receiver and memory 320. As such, in one example implementation, the protocol controller of the RFID tag may be operatively coupled to both the receiver and the memory.

In some example implementations, the antennas 310, 318 may be short in length (e.g., two millimeters) to render the RFID reader 306 and the RFID tag 314 substantially incapable of communication with any other device. However, it should be noted that in other implementations, the antenna may be a length that is not explicitly expressed herein. For example, in one example implementation, the antenna may be substantially longer (e.g., greater than two millimeters) in length. Generally, the antennas may be optimized to minimize the corresponding signal range thereby preventing undesired reading and/or writing communication to and from devices other than the RFID reader 306 and RFID tag 314 (including general RFID readers and RFID tags that are external to the aerosol delivery device 100). The antennas may be, or include, a monopole antenna, dipole antenna, differential antenna or other similarly appropriate antenna.

In alternate example implementations, the power emitted by either the RFID reader 306 and/or the RFID tag 314 may be limited to render the RFID reader and the RFID tag substantially incapable of communication with any other device. In one implementation, for example, the RFID tag may be solely powered via the RFID reader such that the power of the RFID reader may be limited thereby disabling an RFID tag that is external to the aerosol delivery device 100 from being powered.

In some example implementations, the communication between the RFID reader 306 and the RFID tag 314 includes an authentication indicia communicated from the RFID tag to the RFID reader in which the RFID tag is configured to automatically communicate the authentication indicia to the RFID reader upon coupling of the control body 102 with the cartridge 104. The control component 208 may be configured to authorize the cartridge in response to automatically receiving the authentication indicia from the RFID tag via the RFID reader upon coupling the control body with the cartridge. The control body may further automatically evaluate the authentication indicia to determine whether the cartridge is authorized for use with the control body in which the cartridge in at least one instance may be authorized for use with the control body. In some example implementations, the RFID reader and/or the RFID tag may comprise integrated security parameters to prevent undesired reading and/or writing communication to and from devices other than the RFID reader 306 and RFID tag 314 (including general RFID readers and RFID tags that are external to the aerosol delivery device 100). In one implementation, for example, data stored within the RFID tag may be encrypted.

Suitable authentication of the cartridge 104 for use with the control body 102 may involve, in one example implementation, a determination as to whether the cartridge is produced by the manufacturer of the control body (i.e., the control body may only be used with a cartridge manufactured or authorized by the same manufacturer of the control body). In another example implementation, authentication may involve a determination of whether the cartridge may be within a corresponding series authorized for use with the control body (i.e., the control body is configured for use only with Series X, Y, or Z cartridges, wherein a Series N cartridge would not be configured to provide a suitable authentication indicia to allow that cartridge to be used with the noted control body).

Accordingly, in some example implementations, the control component 208 may be configured to be responsive to the received authentication indicia from the engaged cartridge 104, authorizing the particular cartridge for use with the control body 102, to allow current flow from the electrical power source to at least one heating element of the cartridge. As such, the control component is configured to enable current flow and thereby activation of the heating element in the at least one instance in which the cartridge is authorized for use with the control body, and prohibit the current flow and thereby activation of the heating element in at least one other instance in which the cartridge is unauthorized for use with the control body. For example, if no authentication indicia is received by the control component (i.e., an absent authentication indicia) or if an unauthorized authentication indicia is received by the control component, the control component may respond, for example, by prohibiting or preventing current flow from an electrical power source of the control body to the at least one heating element of the cartridge.

Figure 4:
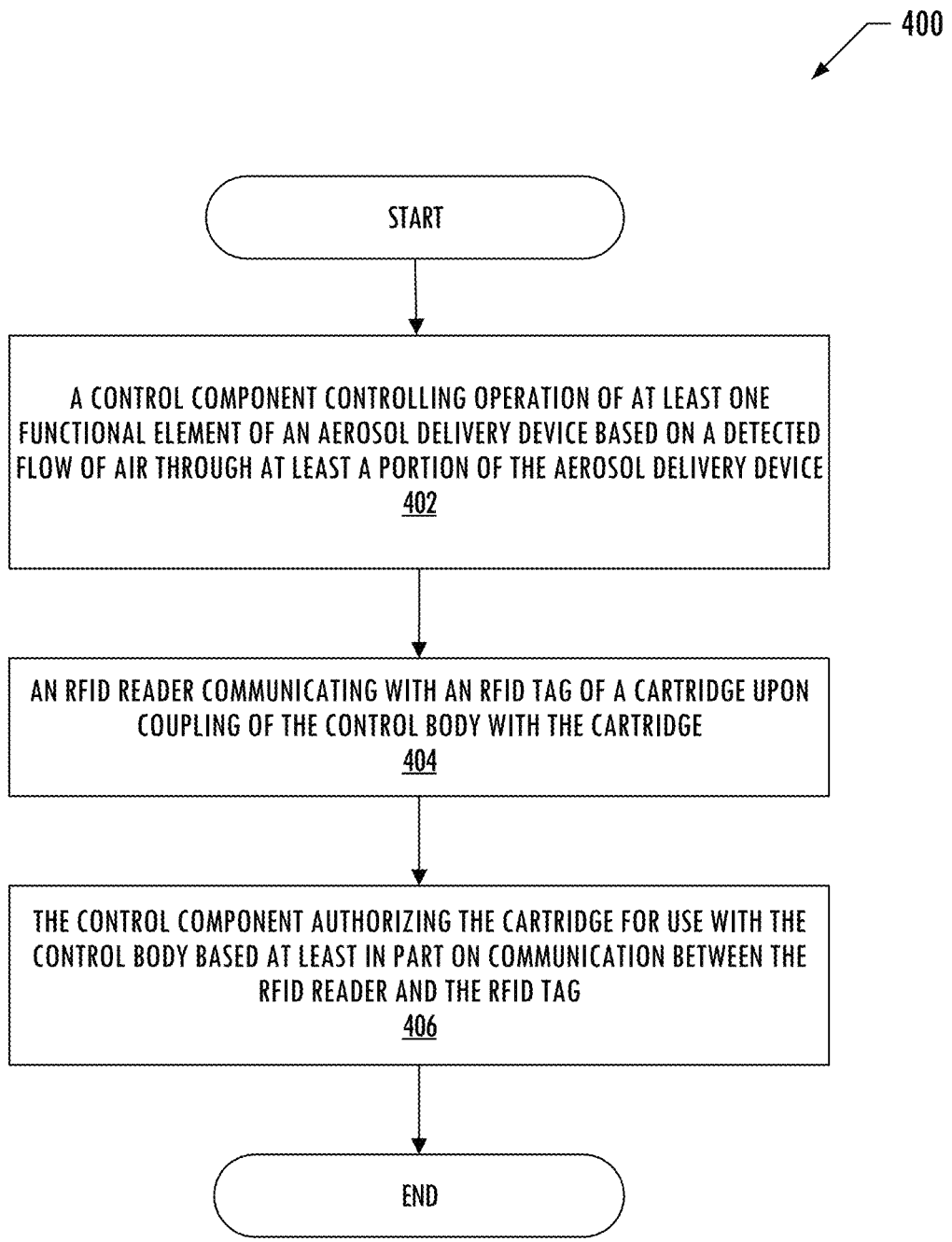
FIG. 4 illustrates various operations in a method of operation of an aerosol delivery device control body, according to an example implementation of the present disclosure.

FIG. 4 illustrates various operations in a method 400 of operation of a control body. The control body may be coupleable with a cartridge that is equipped with a heating element and contains an aerosol precursor composition, and is further equipped with a RFID tag. The control body may be coupleable with the cartridge to form an aerosol delivery device in which the heating element is configured to activate and vaporize components of the aerosol precursor composition. As shown at block 402, the method may include a control component controlling operation of at least one functional element of the aerosol delivery device based on a detected flow of air through at least a portion of the aerosol delivery device. As shown at block 404, the method may also include an RFID reader communicating with the RFID tag of the cartridge upon coupling of the control body with the cartridge. As shown at block 406, the method may also include the control component authorizing the cartridge for use with the control body based at least in part on communication between the RFID reader and the RFID tag.

FIG. 5 illustrates various operations in a method 500 of operation of a cartridge. The cartridge may be coupleable with a control body equipped with a RFID reader. The cartridge may be coupleable with the control body to form an aerosol delivery device. As shown at block 502, the method may include a heating element activating to vaporize components of an aerosol precursor composition in response to a flow of air through the aerosol delivery device in which the air may be combinable with a thereby formed vapor to form an aerosol. As shown at block 504, the method may also include an RFID tag communicating with the RFID reader of the control body upon coupling of the cartridge with the control body, which the cartridge is authorized at, for use with the control body based at least in part on communication between the RFID reader and the RFID tag.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-3 or as otherwise described above may be included in an aerosol delivery device according to the present disclosure.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method of operation of an aerosol delivery device that includes a control body coupleable with a cartridge, the cartridge containing an aerosol precursor composition and equipped with a radio-frequency identification (RFID) tag, and the control body comprising at least one housing including a coupler having a cavity, the method comprising:
    coupling the control body with the cartridge such that the cartridge engages the coupler;
    at the control body:
        communicating, using an RFID reader of the control body, with the RFID tag of the cartridge;

authorizing, by a processor of the control body, the cartridge for use with the control body based at least in part on the communication between the RFID reader and the RFID tag; and controlling, by the processor, the aerosol delivery device to produce an aerosol from the aerosol precursor composition contained in the cartridge, wherein the RFID reader or the RFID tag is configured such that power emitted thereby causes the RFID reader or the RFID tag to be incapable of communicating with other devices outside the aerosol delivery device, wherein the RFID reader includes an antenna positioned in the cavity of the coupler such that upon coupling of the control body with the cartridge, the antenna of the RFID reader is located proximate an antenna of the RFID tag to enable the communication between the RFID reader and the RFID tag, and wherein the antenna of the RFID reader is configured to render the RFID reader substantially incapable of communication with any device external to the control body other than the RFID tag.

2. The method of claim 1, wherein the antenna of the RFID reader is up to two millimeters in length to render the RFID reader incapable of communication with any device external to the control body other than the RFID tag.

3. The method of claim 1, wherein the communication between the RFID reader and the RFID tag includes an authentication indicia communicated from the RFID tag to the RFID reader, and the processor authorizing the cartridge includes automatically:

at the control body:

receiving the authentication indicia from the RFID tag via the RFID reader upon coupling the control body with the cartridge; and evaluating the authentication indicia to determine whether the cartridge is authorized for use with the control body.

4. The method of claim 3, wherein the aerosol delivery device includes a heating element configured to activate and vaporize components of the aerosol precursor composition to produce the aerosol, the method further comprising:

at the control body:

in response to the cartridge being authorized for use with the control body, the processor enabling current flow and thereby activation of the heating element; and in response to the cartridge not being authorized for use with the control body, the processor prohibiting the current flow and thereby activation of the heating element.

5. The method of claim 1, wherein the RFID reader includes a radio-frequency amplifier driving the antenna of the RFID reader, the method further comprising:

at the control body:

the radio-frequency amplifier operating at a power level of at least one-hundred milliwatts to enable an emission of energy sufficient to at least partially power the RFID tag.

6. The method of claim 1, wherein the method further comprises:

at the cartridge:

the RFID tag communicating with the RFID reader of the control body upon coupling of the cartridge with the control body to authorize use of the cartridge with the control body; and providing the aerosol precursor composition to the aerosol delivery device to produce the aerosol.

7. The method of claim 6, further at the cartridge:

wherein the antenna of the RFID tag is contained within the cartridge such that upon coupling of the control body with the cartridge, the antenna of the RFID tag is located proximate the antenna of the RFID reader to enable the communication between the RFID reader and the RFID tag, and wherein the antenna of the RFID tag is up to two millimeters in length to render the RFID tag incapable of communication with any device external to the cartridge other than the RFID reader.

8. The method of claim 6, wherein the communication between the RFID tag and the RFID reader includes an authentication indicia communicated from the RFID tag to the RFID reader, and the method further comprises:

further at the cartridge:

the RFID tag automatically communicating the authentication indicia to the RFID reader upon coupling of the control body with the cartridge, the authentication indica to be sent to the processor of the control body for evaluating if the cartridge is authorized for use with the control body.

9. The method of claim 8, further comprising:

at the cartridge:

in response to the cartridge being authorized by the processor for use with the control body, receiving current flow to a heating element at the cartridge, thereby activating the heating element to vaporize components of the aerosol precursor composition to produce the aerosol, and in response to the cartridge being unauthorized by the processor for use with the control body, not receiving current flow to the heating element.

10. The method of claim 6, wherein the cartridge is a disposable cartridge with flavor-containing aerosol precursor composition, and the RFID tag includes a memory, and wherein the method further comprises:

at the memory of the RFID tag of the cartridge:

storing information related to a capacity of the cartridge or flavor of the flavor-containing aerosol precursor composition; and storing data related to a puff count associated with the cartridge.

* * * * *